United States Patent
Kang et al.

(10) Patent No.: US 8,175,687 B2
(45) Date of Patent: May 8, 2012

(54) LIGHT SOURCE FOR FLUORESCENCE DIAGNOSIS AND PHOTODYNAMIC THERAPY

(75) Inventors: Uk Kang, Gunpo-si (KR); Garri Papayan, Saint Petersburg (RU); Soo Jin Bae, Sangnok-gu (KR); Geun Hie Rim, Changwon-si (KR)

(73) Assignee: Korea Electro Technology Research Institute, Gyeongsangnam-do (KR)

( * ) Notice: Subject to any disclaimer, the term of this patent is extended or adjusted under 35 U.S.C. 154(b) by 993 days.

(21) Appl. No.: 12/096,029

(22) PCT Filed: Dec. 5, 2006

(86) PCT No.: PCT/KR2006/005206
§ 371 (c)(1),
(2), (4) Date: Jun. 4, 2008

(87) PCT Pub. No.: WO2007/111408
PCT Pub. Date: Oct. 4, 2007

(65) Prior Publication Data
US 2008/0269576 A1  Oct. 30, 2008

(30) Foreign Application Priority Data
Mar. 29, 2006  (KR) .................. 10-2006-0028367

(51) Int. Cl.
*A61B 6/00* (2006.01)

(52) U.S. Cl. ...................... 600/473; 600/476

(58) Field of Classification Search .............. None
See application file for complete search history.

(56) References Cited

U.S. PATENT DOCUMENTS

| 4,556,057 | A  | * | 12/1985 | Hiruma et al. ............. 600/476 |
| 5,507,287 | A  |   | 4/1996  | Palcic et al. |
| 5,749,830 | A  | * | 5/1998  | Kaneko et al. ............. 600/160 |
| 5,851,181 | A  | * | 12/1998 | Talmor ..................... 600/407 |
| 5,877,806 | A  | * | 3/1999  | Kawano .................... 348/219.1 |
| 6,212,425 | B1 | * | 4/2001  | Irion et al. ................ 600/476 |
| 6,214,033 | B1 | * | 4/2001  | Ii et al. .................... 607/89 |
| 6,383,175 | B1 | * | 5/2002  | Ii et al. .................... 606/3 |
| 6,640,131 | B1 | * | 10/2003 | Irion et al. ................ 600/476 |
| 6,975,898 | B2 | * | 12/2005 | Seibel ...................... 600/473 |

(Continued)

FOREIGN PATENT DOCUMENTS
JP  2005-211272  11/2005

*Primary Examiner* — Long V. Le
*Assistant Examiner* — Angela M Hoffa
(74) *Attorney, Agent, or Firm* — Whitham Curtis Christofferosn & Cook, PC

(57) ABSTRACT

Disclosed herein is a light source device for fluorescence diagnosis and photodynamic therapy comprising: a plurality of light source means having a wavelength range different from each other and providing selected light; a light path coupling means coupling light emitted from the light source means to the incident direction of a light guide; a filtering means selectively transmitting the emitted light based on the wavelength; and a switching device that is directed to an opening/closing means, established at a long distance to be controlled by a remote control device and selecting the kinds of light sources of the light source means to change the modes of the light. Accordingly, the device simplifies the configuration by excluding elements causing errors in the process of fluorescence diagnosis in the diagnostic region. Moreover, the light source device for fluorescence diagnosis and photodynamic therapy couples the light emitted from a combined light source to provide a sufficient light strength in the visible light region, thus improving the illumination quality to increase the accuracy of the diagnosis and further improving the therapeutic efficiency.

18 Claims, 3 Drawing Sheets

U.S. PATENT DOCUMENTS

| | | |
|---|---|---|
| 7,016,718 B2 * | 3/2006 | Ii et al. ............ 600/475 |
| 7,635,330 B2 * | 12/2009 | Kang et al. ............ 600/160 |
| 2002/0062061 A1 * | 5/2002 | Kaneko et al. ............ 600/118 |
| 2003/0036785 A1 * | 2/2003 | Ii et al. ............ 607/89 |
| 2003/0060719 A1 * | 3/2003 | Irion et al. ............ 600/476 |
| 2003/0078477 A1 | 4/2003 | Kang et al. |
| 2004/0230098 A1 * | 11/2004 | Farkas et al. ............ 600/178 |
| 2005/0203343 A1 * | 9/2005 | Kang et al. ............ 600/160 |
| 2006/0241496 A1 * | 10/2006 | Fengler et al. ............ 600/476 |
| 2007/0015963 A1 * | 1/2007 | Fengler et al. ............ 600/109 |
| 2009/0099459 A1 * | 4/2009 | Svanberg et al. ............ 600/478 |
| 2010/0185099 A1 * | 7/2010 | Johansson et al. ............ 600/473 |

* cited by examiner

① DICHROIC MIRROR TRANSMITTED SPECTRUM
② LIGHT SPECTRUM OF MERCURY LAMP
③ LIGHT SPECTRUM OF HALOGEN LAMP
④ LIGHT SPECTRUM COUPLED ON BOUNDARY SURFACE OF DICHROIC MIRROR

LIGHT SOURCE FOR FLUORESCENCE DIAGNOSIS AND PHOTODYNAMIC THERAPY

TECHNICAL FIELD

The present invention relates to a light source for fluorescence diagnosis and photodynamic therapy and, more particularly, to a light source device for fluorescence diagnosis and photodynamic therapy that increases diagnostic accuracy of skin diseases, especially, tumor diagnoses, and improves phototherapeutic efficiency in connection with a combined light source technique for the diagnosis and therapy of the skin diseases.

BACKGROUND ART

For the purpose of the diagnosis and treatment of diseases using light, optical fiber light sources based on various types of lamps such as halogen, xenon, metal-halide, mercury, etc. that are generally well-known have been used.

Such lamps have been selected based on technical and economic considerations, as well as on considerations for the special medical purposes of the devices and on manufacturing demands.

However, a single lamp applied thereto has not provided an optimal method in a case where a complex operation that needs various lights of a wide range or of a selective wavelength band is required.

In such a case, the device developer depends on a lamp having a special function or uses a plurality of lamps at the same time, thus overcoming the weak points.

Especially, it is known that the observation of geometry, position, and color of a diagnostic region by white light is essential in addition to the observation of fluorescence generated from the diagnostic object by the excitation light irradiation in diagnosing diseases using fluorescence.

In order to develop devices for diagnosing diseases through fluorescence generated in the diagnostic region, researchers have solved such problems via respective various methods.

For example, Karl Storz GmbH & Co. KG (Germany) uses a D-light xenon lamp that is a light source manufactured by itself.

Such a lamp provides good conditions for the observation in the white light if it has bright successive spectrums in a visible light region.

However, it causes an excitation energy loss for the fluorescence observation in a short wavelength range of 350 to 550 nm.

Xillix Technologies Corp. (Canada) uses a mercury lamp in its Onco-LIFE device. As is well known in the art, it is advantageous in the fluorescence emission from the diagnostic region to use the excitation light due to strong light beams in a spectrum of a short wavelength range rather than the other light sources.

However, the bright line spectrums of the light emitted from such a lamp make it difficult to provide a normal observation for the diagnostic object under the white light condition.

A light source of LumaCare (USA) developed for the execution of photodynamic therapy (PDT) uses a halogen lamp.

In this case, since the light strength of spectrum in a short wavelength range is not large, it cannot provide sufficient light strength permissible for phototherapy.

Like this, in the case where the single lamp is applied to the light source device, it is difficult to provide optimal conditions that satisfy various demands for the diagnosis and therapy.

Korean Patent No. 10-0411631 discloses a light source device using two lamps to improve the illumination quality in a fluorescence diagnosis device.

In the above-mentioned light source device, two lamps composed of a halogen lamp and a mercury lamp are established and the incident light from the two lamps are irradiated in turn on the end of the input surface of a light guide depending on a foldable mirror.

That is, according to the positions of the mirror, the excitation light emitted from the mercury lamp or the white light emitted from the halogen lamp is irradiated onto the light guide incident surface.

However, such a light source device has drawbacks in that the volume of the light source device becomes larger as it includes a foldable mirror driving unit and a control block and unnecessary heat is generated from the driving unit.

Furthermore, if the mirror does not reach a position in a proper angle, the light amount reflected by the mirror becomes smaller.

DISCLOSURE

Accordingly, the present invention solves the above-described drawbacks, and an object of the present invention is to improve the operational reliability of the light source device and further simplify the configuration. The invention uses a fixed light path coupling means for coupling or dividing the light emitted from two light sources which are different from each other. The fixed light path coupling means forwards the light from the two light sources to the light guide for the purposes of white light observation and fluorescence diagnosis in the diagnostic region, and does so differently from the conventional foldable minor that causes errors in the diagnostic process.

Another object of the present invention is to provide a light source device that couples the light emitted from the two different light sources through the light path coupling means under the white light condition for observing the diagnostic region to provide a sufficient light strength in the visible light region, thus improving the illumination quality to increase the accuracy of the diagnosis and, at the same time, increasing the light strength in the short wavelength region in the process of the phototherapy to improve the therapeutic efficiency.

Moreover, another object of the present invention is to provide a light source device that improves the operational reliability as the illumination conditions can be changed only with the operation of the switching device without changing the positions of the optical modules configured to convert the white light condition into the excitation light condition and vice versa.

To accomplish the above objects of the present invention, there is provided a light source device for fluorescence diagnosis and photodynamic therapy comprising: a plurality of light source means having a wavelength range different from each other and providing selected light; a light path coupling means coupling light emitted from the light source means to the incident direction of a light guide; a first filtering means mounted in a single case along with the light path coupling means and selectively transmitting the emitted light based on the wavelength; a light guide guiding the light to a diagnostic region; and a switching device that is directed to an opening/closing means, established at a long distance to be controlled by a remote control device and selecting the kinds of light sources of the light source means to change selection conditions of the light source device.

Hereinafter, the configuration of the present invention will be described with reference to the attached drawings.

The attached FIG. 1 is a configuration diagram depicting a light source device for fluorescence diagnosis and photodynamic therapy in accordance with the present invention, FIGS. 2 to 4 are configuration diagrams depicting light source devices embodied for the white light condition, the excitation light condition and the photodynamic therapy condition in accordance with the present invention, and FIG. 5 is a graph showing light spectrum curves of the respective light sources, a dichroic mirror and lamps coupled by the dichroic mirror.

The light source device in accordance with the present invention comprises a plurality of light source means 10 which provides light at different selected wavelengths using different sources that have a wavelength range different from each other. The light source device uses non-coherent light source means 10 and emits white light to observe a general diagnostic region 1, excitation light to perform fluorescence diagnosis, or light in a predetermined light spectrum region to carry out photodynamic therapy (PDT).

Here, the excitation light emitted from the selected light source means 10 is generated in an excitation light source 11 having a main light in a short wavelength range of spectrum. The white light is irradiated through a fixed dichroic mirror 21 that is a light path coupling means 20 for coupling the light emitted from a long wavelength light source 12 having a main light in a long wavelength range of spectrum and the light emitted from the excitation light source 11 in the incident surface direction of a light guide 50.

It is possible to change the angle of the incident surface of the dichroic mirror 21 to control the incident light from the excitation light source 11 and the long wavelength light source 12, respectively. In general, the angle of the incident surface of the dichroic mirror 21 is set at 45° and the excitation light of the excitation light source 11 is transmitted through the dichroic mirror 21 and irradiated through the light guide 50 and, at the same time, the white light of the long wavelength light source 12 is reflected at 90° to be irradiated through the light guide 50.

Here, the excitation light source 11 for the excitation light may use a mercury lamp and the long wavelength light source 12 emitting the main light in the long wavelength range may use a halogen lamp, a xenon lamp, a metal-halide lamp or a light emitting diode.

Meanwhile, an oval reflecting mirror may be used to collect the light emitted from the light sources 11 and 12 and concentrate the same to the light guide 50. The reflecting mirror is subjected to a dichroic coating to send light of undesirable infrared rays (IR) spectrum generated from the light sources 11 and 12 to the rear surface of the reflecting mirror.

Alternatively, it is possible to send the light to the light guide 50 using a condenser instead of the reflecting mirror.

Moreover, it is possible to convert the light emitted from the light sources 11 and 12 into parallel light beams using a collimator and supply the same to the light guide 50 through a first filtering means 30.

In this case, an object lens that collects parallel light beams and sends the same to the light guide 50 may be additionally established between the dichroic mirror 21 and the light guide 50.

The above-described configuration of the light source device can be considered a generalized configuration and a condenser or collimator may be added to or removed from the light source device based on its configuration.

It is desirable that the excitation light for examining skin diseases, especially, acne's state, should include a spectrum range of 380 to 460nm, and autofluorescence according to the excitation light is observed over such a range.

That is, if propionibacterium acnes (P.acnes), known as acne causative microorganisms, exist in pores, orange-red fluorescence (maximum value of fluorescence emission is 635 nm) is emitted by porphyrins produced by the P.acnes, and the fluorescence emitted becomes red as much as the amount of the P.acnes accumulated in the pores is increased.

On the other hand, if the P.acnes become extinct by an antibacterial drug, only green fluorescence (510-570 nm) generated from sebum in the pores is observed instead of the red fluorescence.

Through this, it is possible to readily diagnose the amount of sebum in the pores, whether or not the P.acnes exist, the amount of P.acnes accumulated, the healing state of acnes, etc., and it allows for preventing overdose of the antibacterial drug.

Meanwhile, when observing induced fluorescence using a contrast agent such as 5-ALA (5-aminiolevulinic acid) on an affected region such as skin malignant tumor, it is desirable that the excitation light should have a spectrum range of 380 to 560 nm while the fluorescence generally has a wavelength of more than 600 nm.

However, such a wavelength range may be varied according to the fluorescent contrast agent applied thereto and thereby an appropriate optical system including various filters having wavelength ranges based on the same may be established.

In the optical system, the first filtering means 30 for selectively transmitting the light based on the wavelength is provided in the vicinity of the dichroic mirror 21 positioned in front of the respective lamps, and the first filtering means 30 and the dichroic mirror 21 are mounted in a single case 60 having a predetermined space. Moreover, in the optical system, an excitation filter 31 is established between the excitation light source 11 and the dichroic mirror 21 to transmit a specific wavelength band, i.e., only the fluorescence emission, and a heat protection filter 32 is provided in front of the excitation filter 31 to prevent optical elements positioned on the path of the excitation light from being destroyed due to radiant heat.

Here, if the dichroic mirror 21 could pass only the wavelength band of the excitation light selected from the light emitted from the excitation light source 11, the excitation filter 31 may be unnecessary.

The dichroic mirror 21 used as the light path coupling means 20 has a high light transmittance in a short wavelength range and a low light transmittance in a long wavelength range. Accordingly, the dichroic mirror 21 passes the excitation light of the excitation light source 11 and reflects the light of the long wavelength light source 12.

It is desirable that the dichroic minor 21 should show transmittance characteristics in the spectrum range of the short wavelength of the excitation light source 11 and show reflection characteristics in the long wavelength over the same spectrum range.

A near IR interference filter 33 is established between the long wavelength light source 12 and the dichroic mirror 21 to prevent the near IR emitting light from being projected to a television camera.

Here, the near IR interference filter 33 shields the light of 740 nm or more in order to intercept the near IR emitted light.

FIG. 2 is a configuration diagram depicting a light source device under the white light condition for the observation of the diagnostic region 1 in accordance with an embodiment of the present invention.

The dichroic mirror 21 under the white light condition transmits the excitation light of the excitation light source 11 and, at the same time, reflects the light of the long wavelength light source 12 so as to be coupled and irradiated to the incident surface direction of the light guide 50.

In this case, it is possible to observe the diagnostic region 1 with the light having more uniform and higher output strength than the case where the single light source is used in the visual light spectrum region for observing the diagnostic region 1.

For example, in the light spectrum curves of the respective light sources depicted in FIG. 5, the excitation light emitted from the mercury lamp, i.e., the excitation light source 11, passes through the dichroic mirror 21 showing good light transmittance characteristics up to 450 nm, whereas, the light emitted from the halogen lamp, i.e., the long wavelength light source 12 showing a fixed strength in the red wavelength range of more than 450 nm and, more particularly, more than 600 nm, is reflected in the dichroic mirror 21 showing good reflection characteristics for more than 450 nm.

The excitation light transmitted at less than 450 nm and the light reflected at more than 450 nm are coupled by passing through the dichroic mirror 21, thus providing the light of higher quality than that in the visible light region, as depicted in FIG. 5.

That is, since the light source device in accordance of the present invention provides the white light supplemented in the short wavelength spectrum range rather than the case where only the halogen lamp is used as the conventional white light source, it is possible to improve the illumination quality so as to observe the diagnostic region 1 more readily.

FIG. 3 is a configuration diagram depicting a light source device under the excitation light condition for the fluorescence observation of the diagnostic region 1 in accordance with another embodiment of the present invention.

When irradiating the excitation light for the fluorescence observation onto the diagnostic region 1, the operation of the long wavelength light source 12 is suspended by the switching operation of a switching device 41, i.e., an opening/closing means 40 for changing the selection conditions of the light source device by selecting the kinds of the light sources in the light source means 10. Then, only the light emitted from the excitation light source 11 goes by the excitation filter 31 and the heat protection filter 32 and passes through the dichroic mirror 21 to irradiate the excitation light onto the diagnostic region 1 through the light guide 50.

If the dichroic mirror 21 could pass only the wavelength band of the excitation light selected from the light emitted from the excitation light source 11, the excitation filter 31 may be unnecessary.

Here, the white light condition can be converted into the excitation light condition and vice versa using only the switching operation of the switching device 41.

The switching device 41 may be established at a long distance to be controlled by a remote control device 42.

Accordingly, the present invention excludes the conventional foldable mirror, operated mechanically to convert the excitation light condition into the white light condition and vice versa, and adopts the fixed dichroic mirror, thus simplifying the structure of the light source device and preventing unnecessary heat from being generated by the operation of the driving unit applied thereto. Moreover, the present invention can prevent the amount of the white light reflected from the mirror from becoming smaller as the light irradiation angle of the foldable mirror is not maintained fixedly due to continuous use.

FIG. 4 is a configuration diagram depicting a light source device under the photodynamic therapy condition for the therapy of the diagnostic region 1 in accordance with another embodiment of the present invention.

Under the photodynamic therapy condition, since the light source device of the present invention irradiates coupled light of the excitation light source 11 and the long wavelength light source 12, not the single light of the long wavelength light source 12, it is possible to provide output strength substantially supplemented in the short wavelength range of visible light.

The wavelength range irradiated onto the diagnostic region 1 for the photodynamic therapy is varied according to the kind of disease, the state of disease or the contrast agent applied thereto.

For example, the light in the vicinity of 380 nm to 660 nm is used for acne therapy based on factors such as the development of acne, the depth of skin penetration for the therapy, etc.

If the contrast agent 5-ALA is used, light in the vicinity of 630 nm is used, whereas, if Radachlorine (chlorin e6 photosensitzer) is used, the light in the vicinity of 650 nm is used.

If the light selected for the purpose of the photodynamic therapy is irradiated onto the diagnostic region 1, the light emitted from the excitation light source 11 and the long wavelength light source 12 are coupled in the dichroic mirror 21, i.e., the light path coupling means 20, and a wavelength for the photodynamic therapy is selected from the coupled light through a filter for photodynamic therapy 36, i.e., a second filtering means 35 disposed between the dichroic mirror 21 and the light guide 50.

Here, the filter for photodynamic therapy 36 may be established to be replaced in a platform equipped in a rotating disc device 70.

Figure 1:
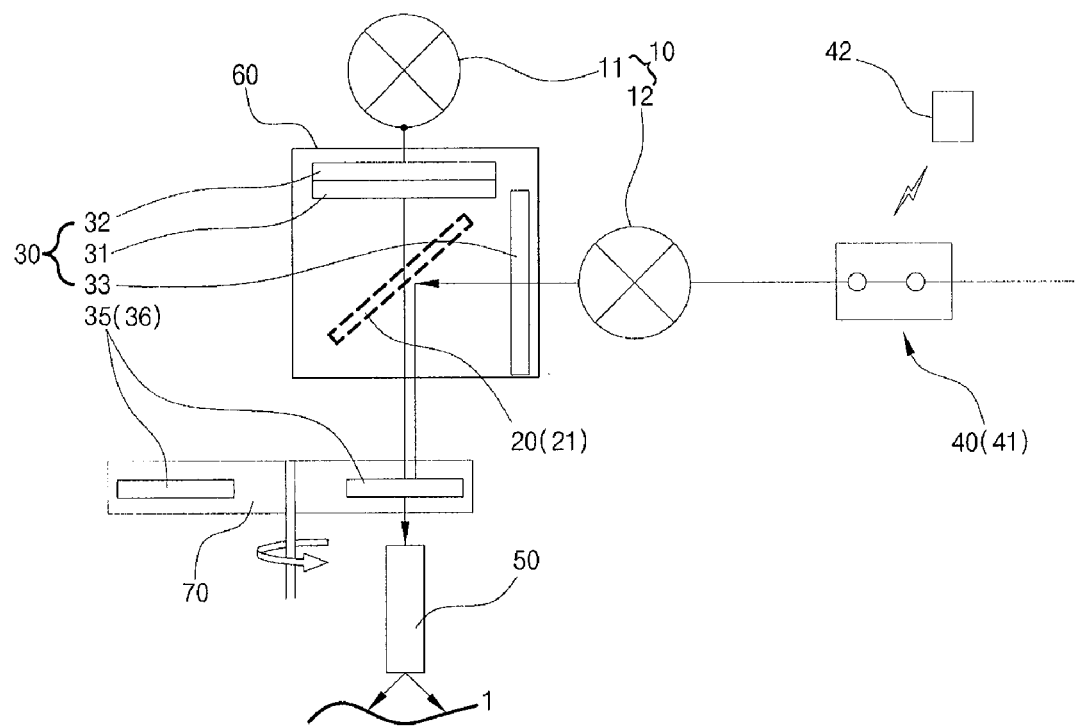
FIG. 1 is a configuration diagram depicting a light source device for fluorescence diagnosis and photodynamic therapy in accordance with the present invention.
Figure 2:
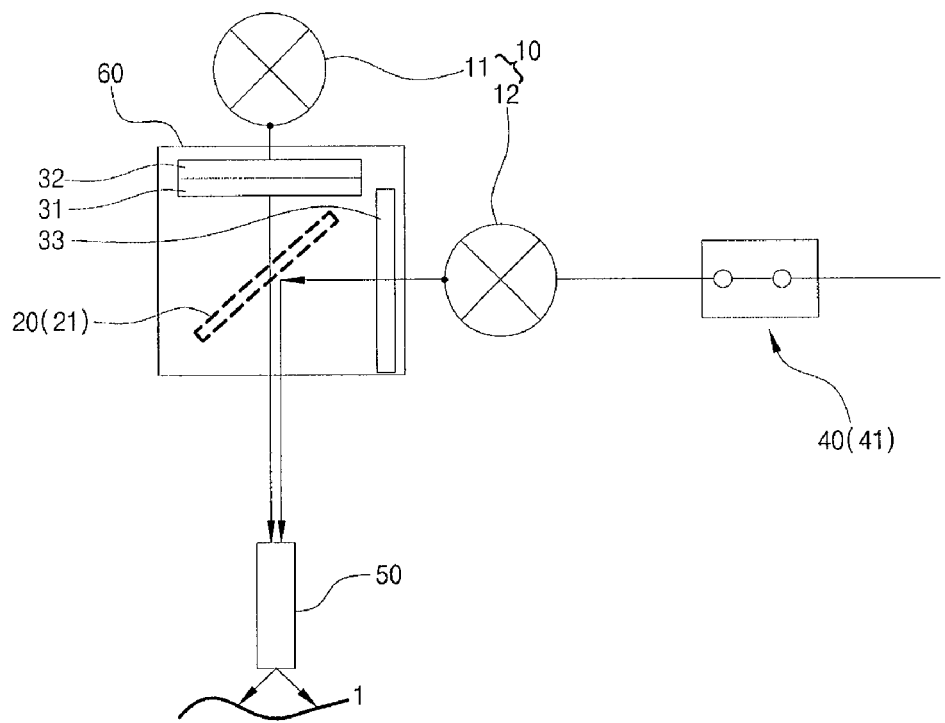
FIG. 2 is a configuration diagram depicting a light source device under the white light condition in accordance with the present invention.
Figure 3:
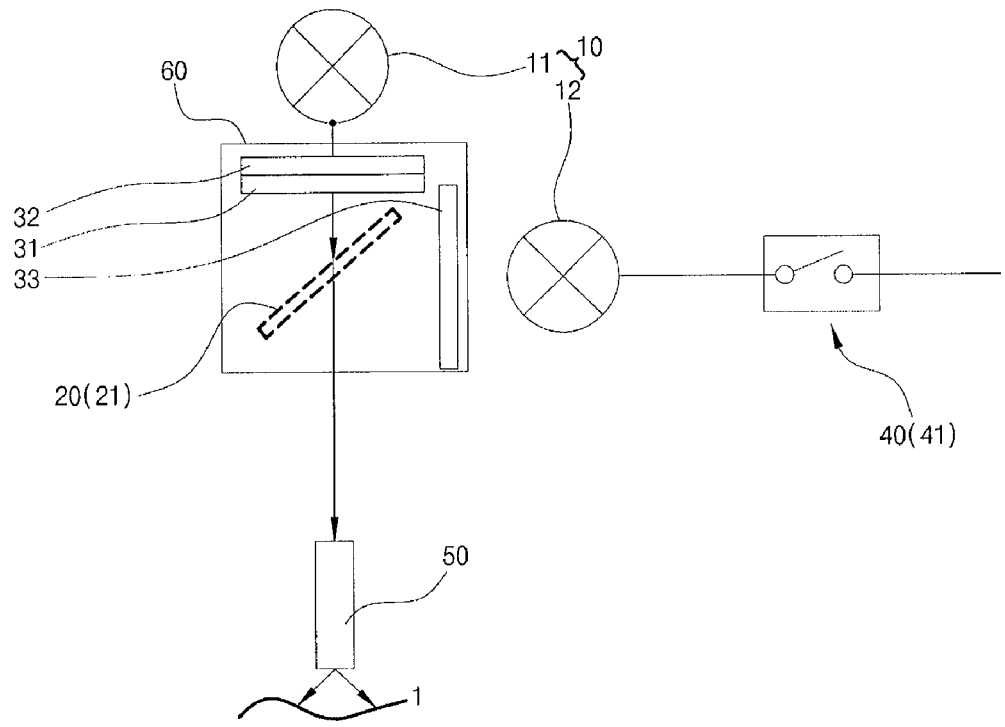
FIG. 3 is a configuration diagram depicting a light source device under the excitation light condition in accordance with the present invention.
Figure 4:
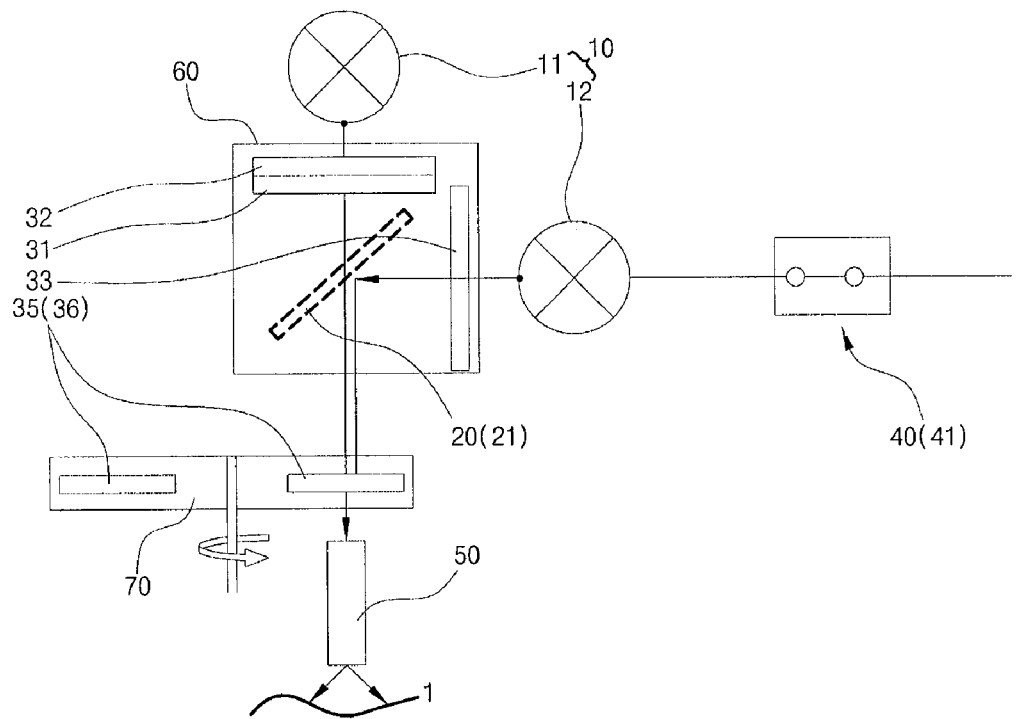
FIG. 4 is a configuration diagram depicting a light source device under the photodynamic therapy condition in accordance with the present invention.
Figure 5:
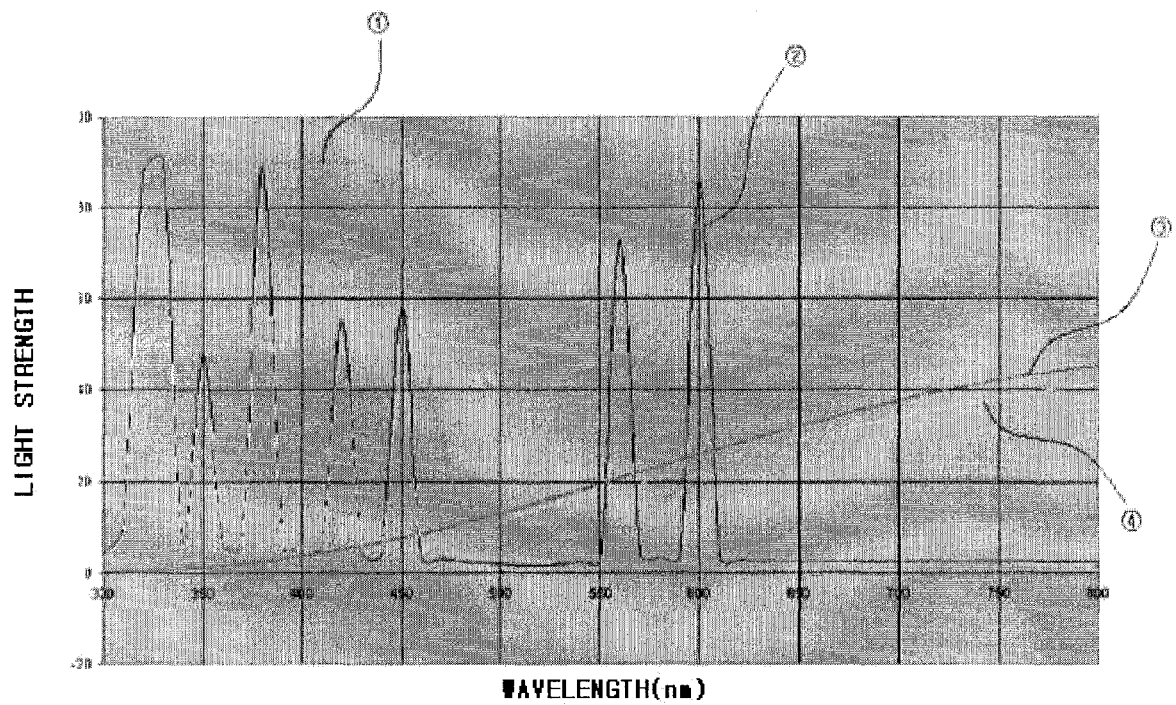
FIG. 5 is a graph showing light spectrum curves of the respective light sources, a dichroic mirror and lamps coupled by the dichroic mirror.

| | |
|---|---|
| 1: | Diagnostic region |
| 10: | Light source means |
| 11: | Excitation light source |
| 12: | Long wavelength light source |
| 20: | Light path coupling means |
| 21: | Dichroic mirror |
| 30: | First filtering means |
| 31: | Excitation filter |
| 32: | Heat protection filter |
| 33: | Near IR interference filter |

-continued

| 35: | Second filtering means |
| 36: | Filter for photodynamic therapy |
| 40: | Closing means |
| 41: | Switching device |
| 42: | Remote control device |
| 50: | Light guide |
| 60: | Single case |
| 70: | Disc device |

Industrial Applicability

As described in detail above, the light source device for fluorescence diagnosis and photodynamic therapy in accordance with the present invention may have an improved illumination quality of white light through the fixed dichroic mirror that is directed to the light path coupling means which couples the light generated from two light sources each having a main light in a different wavelength range. Moreover, it is possible to improve the operational reliability of the light source device and simplify the configuration of the device by using a switching device that passes only the excitation light without changing the dichroic mirror even under the excitation light condition. Furthermore, it is possible to increase the diagnostic accuracy of skin diseases, especially, tumor diagnoses, and improve therapeutic efficiency by improving illumination strength in the short wavelength region required for photodynamic therapy (PDT).

The invention claimed is:

1. A light source device for fluorescence diagnosis and photodynamic therapy comprising:
   a light source comprised of an excitation light source emitting light in a short wavelength range and a long wavelength light source emitting light in a long wavelength range, wherein said short wavelength range is different from said long wavelength range;
   a light guide adapted to guide light to a diagnostic region;
   a light path coupler coupling light emitted from the light source to an incident end of said light guide;
   a first filter for selectively transmitting emitted light based on wavelength;
   a second filter for photodynamic therapy positionable in a light path between the light path coupler and the light guide; and
   a switching device which controls emissions of the long wavelength light source so as to achieve any of (i) a white light condition where both said excitation light and said long wavelength light are directed to said diagnostic region, (ii) an excitation condition where only said excitation light is directed to said diagnostic region, and (iii) a photodynamic condition where both said excitation and said long wavelength light are directed to said diagnostic region under a photodynamic therapy condition.

2. The light source device for fluorescence diagnosis and photodynamic therapy as recited in claim 1,
   wherein the excitation light source is a mercury lamp.

3. The light source device for fluorescence diagnosis and photodynamic therapy as recited in claim 1,
   wherein the long wavelength light source is selected from the group consisting of a halogen lamp, a light emitting diode, a xenon lamp and a metal-halide lamp.

4. The light source device for fluorescence diagnosis and photodynamic therapy as recited in claim 1,
   wherein the light path coupler is a dichroic mirror that transmits excitation light emitted from the excitation light source and, at the same time, reflects light emitted from the long wavelength light source so as to couple the excitation light together with the light emitted from the long wavelength light source to the incident end of the light guide.

5. The light source device for fluorescence diagnosis and photodynamic therapy as recited in claim 4,
   wherein the dichroic mirror that transmits the excitation light emitted from the excitation light source has a high light transmittance in a light spectrum range of less than 460 nm, thereby enabling a detector to observe fluorescence generated from acne.

6. The light source device for fluorescence diagnosis and photodynamic therapy as recited in claim 4,
   wherein the dichroic mirror that transmits the excitation light emitted from the excitation light source has a high light transmittance in a light spectrum range of less than 560 nm, thereby enabling a detector to observe fluorescence produced from a malignant tumor.

7. The light source device for fluorescence diagnosis and photodynamic therapy as recited in claim 4,
   wherein the dichroic mirror is angled at a 45° with respect to the excitation light and the long wavelength light.

8. The light source device for fluorescence diagnosis and photodynamic therapy as recited in claim 1
   wherein the first filter comprises:
   an excitation filter, established between the excitation light source and the light path coupler, for transmitting only the excitation light;
   a heat protection filter, provided in front of the excitation filter to prevent optical elements; and
   a near infrared ray interference filter, established between the long wavelength light source and the light path coupler to intercept near infrared ray emitting light.

9. The light source device for fluorescence diagnosis and photodynamic therapy as recited in claim 8,
   wherein the excitation filter transmits wavelengths from 380 to 460 nm.

10. The light source device for fluorescence diagnosis and photodynamic therapy as recited in claim 8,
    wherein the excitation filter transmits wavelengths from 380 to 560 nm.

11. The light source device for fluorescence diagnosis and photodynamic therapy as recited in claim 8,
    wherein the near infrared ray interference filter shields light of more than 740 nm.

12. The light source device for fluorescence diagnosis and photodynamic therapy as recited in claim 1,
    wherein the light path coupler and the first filter are both positioned in a single housing.

13. The light source device for fluorescence diagnosis and photodynamic therapy as recited in claim 1, wherein the second filter includes a platform equipped in a rotating disc device.

14. The light source device for fluorescence diagnosis and photodynamic therapy as recited in claim 13,
    wherein the second filter has a high light transmittance in a spectrum range of 380 to 660 nm.

15. light source device for fluorescence diagnosis and photodynamic therapy as recited in claim 13,
    wherein the second filter for photodynamic therapy has a high light transmittance in a spectrum range of 630 to 650 nm.

16. The light source device for fluorescence diagnosis and photodynamic therapy as recited in claim 1,
    wherein the second filter has a high light transmittance in a spectrum range of 380 to 660 nm.

17. The light source device for fluorescence diagnosis and photodynamic therapy as recited in claim 1,
   wherein the second filter has a high light transmittance in a spectrum range of 630 to 650 nm.

18. The light source device for fluorescence diagnosis and photodynamic therapy as recited in claim 1,
   wherein the light path coupler is a dichroic mirror that transmits excitation light emitted from the excitation light source and, at the same time, reflects light emitted from the long wavelength light source so as to couple the excitation light together with the light emitted from the long wavelength light source to the incident end of the light guide.

\* \* \* \* \*